US00PP12025P2

(12) United States Plant Patent
Paquette

(10) Patent No.: US PP12,025 P2
(45) Date of Patent: Jul. 31, 2001

(54) SPIRAEA PLANT NAMED 'GOLDEN ELF'

(76) Inventor: Clément Paquette, Pépiniere Mont-Yamaska Inc., 830, rang de la Montagne, St-Paul-d'Abbotsford, Quebec (CA), JOE 1A0

( * ) Notice: Subject to any disclaimer, the term of this patent is extended or adjusted under 35 U.S.C. 154(b) by 0 days.

(21) Appl. No.: 09/270,832

(22) Filed: Mar. 18, 1999

(51) Int. Cl.[7] ..... A01H 5/00
(52) U.S. Cl. ..... Plt./226
(58) Field of Search ..... Plt./226

(56) References Cited

U.S. PATENT DOCUMENTS

P.P. 7,537 * 5/1991 Catt ..... Plt./226
P.P. 9,363 * 11/1995 Tristram ..... Plt./226

* cited by examiner

*Primary Examiner*—Bruce R. Campell
*Assistant Examiner*—Kent L. Bell
(74) *Attorney, Agent, or Firm*—Mark P. Bourgeois

(57) ABSTRACT

A new and distinct variety of *Spiraea japonica* named 'Golden Elf' that is characterized by a dwarf plant habit, a miniature aspect of the leaves, attractive golden leaf coloration from spring to first frost, a smooth and compact canopy, disease and insect tolerance and does not flower. The new variety is particularly interesting as a hardy outdoor ground cover for garden decoration and landscape use.

1 Drawing Sheet

BACKGROUND OF THE INVENTION

The present invention relates to a new and distinct variety of *Spiraea japonica* that originated as a naturally occurring branch mutation discovered by the inventor on a plant of *Spiraea japonica* 'Goldmound' (not patented) in a cultivated area of St.-Paul d'Abbotsford, Quebec, Canada. The first asexual reproduction of the new cultivar was by softwood cuttings taken by the inventor in St.-Paul d'Abbotsford, Quebec, Canada. 'Golden Elf' was propagated by softwood cuttings and the best young plant selections were chosen for evaluation. This selection process was repeated twice more until a final selection was chosen. Thus, the hundred of plants obtained have shown that the unique features of this new Spiraea are stabilized and are reproduced true to type in successive propagations.

SUMMARY OF THE INVENTION

The new variety 'Golden Elf' was observed over four subsequent years to determine the stability of characteristics and growing behavior in plant container production, plant field production and landscaping. The following observations, measurements, values and comparisons describe the plants as grown in St.-Paul-d'Abbotsford, Quebec, Canada under outdoor conditions that generally exist in commercial horticulture and also closely resemble conditions in garden practice.

The following characteristics have been repeatedly observed and are determined to be basic characteristics of 'Golden Elf', which in combination, distinguish this Spiraea from the cultivar 'Goldmound' and distinguish it as a new and distinct cultivar:

1. A dwarf plant habit. Plants of 'Goldmound' are generally six times as tall as plants of 'Golden Elf'. 'Golden Elf' therefore has a ground cover type habit as an attribute.

2. A miniature aspect of leaves. Leaves of plants of 'Golden Elf' are four times smaller than leaves of 'Goldmound'.

3. An attractive golden leaf coloration. Leaves of plants of 'Golden Elf' maintain their golden color from spring to first frost, especially if grown in full sun. As compared to the leaves of the cultivar 'Goldmound' which only retains its attractive golden leaf color until the end of the summer. During the fall period, the leaves of 'Goldmound' become dull and dark, regardless of light level.

4. A smooth and compact aspect to the canopy. The nature of the canopy of 'Goldmound' is rough and more open.

5. Disease and insect tolernace. Plants of 'Golden Elf' are definitely less affected by diseases and insects than the cultivar 'Goldmound'.

6. Golden Elf does not produce flowers. Plants of 'Goldmound' exhibit a profuse flowering habit.

The new variety has exhibited good hardiness and has survived without injury when overwintered in containers above ground and in the landscape in St-Paul-d'Abbotsford. 'Golden Elf' is considered hardy to Canadian zone 3 (−34.5° to −40° C.).

A detailed camparison of the cultivars 'Golden Elf' and 'Goldmound' appears in Table A at the end of the specification.

BRIEF DESCRIPTION OF THE DRAWING

The accompanying photographs illustrate the overall appearance of the new variety, showing the colors as true as it is reasonably possible by conventional photography.

The photograph at the top of sheet one shows a detailed view of the leaves of 'Golden Elf'.

The bottom photo on sheet one is a photograph of three plants of 'Golden Elf' that illustrate growth throughout the growing season and the consistency of the foliage.

BOTANICAL DESCRIPTION OF THE PLANT

The following description of the new cultivar is based on five year old plants grown in the landscape and on two year old plants produced in containers in St-Paul-d'Abbotsford. Plants were grown under outdoor conditions with average day temperatures ranging from 10° to 28° C. and average night temperatures ranging from 6° to 18° C. from April to November. Color references are made to The Royal Horticultural Society Colour Chart except where general color terms of ordinary dictionary significance are used.

Type: Hardy outdoor ground cover for garden decoration and landscape use.

Botanical classification: *Spiraea japonica* cultivar 'Golden Elf'.

Parentage: A naturally occurring branch mutation of *Spiraea japonica* 'Goldmound' (not patented).

Propagation:

*A. Type.*—By softwood cuttings.

*B. Time to initiate roots, summer.*—10 to 12 days at temperatures of 25° to 30° C.

*Time to develop roots, summer.*—45 to 50 days at temperatures of 25° to 30° C.

*C. Root description.*—Fibrous and branching.

Crop time: A 2 gallon container from a 2½" rooted plug will finish in 12 months when grown outdoors.

Plant description:

*A. General appearance.*—Deciduous ground cover. Low growing (15 to 20 cm) and spreading habit. In the northern hemisphere, shoots are brown and leaves are bright gold especially under full sunlight. Under partial shade, mature leaves are simply gold RHS number upper 2A, lower 2B; under dense shade, mature leaves are greenish gold RHS number upper 149B, lower 149C. Does not produce flowers.

*B. Stem description.*—Habit. — Upright and zigzag twig character. All lateral stems grow in an upright habit giving a shaggy mat aspect. Color. — Young and mature stems are in the greyed-orange group, 175A. Length. — 12–18 cm. Diameter. — 0.75–1.5 mm Texture. — Glabrous. Internode Length. — 0.5 to 1.0 cm.

*C. Foliage description.*—Type. — Deciduous. The leaves are not exactly typical of the species, they are egg-shaped with an obtuse base and apex. Serration is single and fairly regular. Young leaves are concave along central vein and mature leaves are flat. Leaf texture is smooth and veins a little prominent on the under side. Petiole. — Small, approximately 1.5 to 2 mm on average on both young and mature leaves. The young petiole coloration is in the greyed-red group, 179C and mature petiole coloration is in the greyed-orange group, 175A. Color. — Upper side of young and mature leaves fully expanded are in the yellow group 2A and under side are in the yellow group 2B.

*D. Flowers.*—Does not produce flowers.

*E. Disease resistance.*—Diseases such as cylindrosporian and septorian leaf spots are very seldom observed Aphid infestation is rarely observed as well.

*F. Fruit.*—Fruit production has not been observed.

TABLE A

| DIMENSIONS | 'GOLDEN ELF' | 'GOLDMOUND' |
|---|---|---|
| PLANT HEIGHT (cm) | 15–20 | 90–110 |
| PLANT WIDTH (cm) | 50–60 | 105–115 |
| PETIOLE LENGTH (mm) | 1.5–2.0 | 1.5–2.0 |
| PETIOLE DIAMETER (mm) | 0.5–1.0 | 1.0–1.5 |
| LEAF LENGTH (mm) | 8–11 | 44–47 |
| LEAF WIDTH (mm) | 5–6 | 20–24 |

I claim:

1. A new and distinct cultivar of *Spiraea japonica* plant named 'Golden Elf', as illustrated and described.

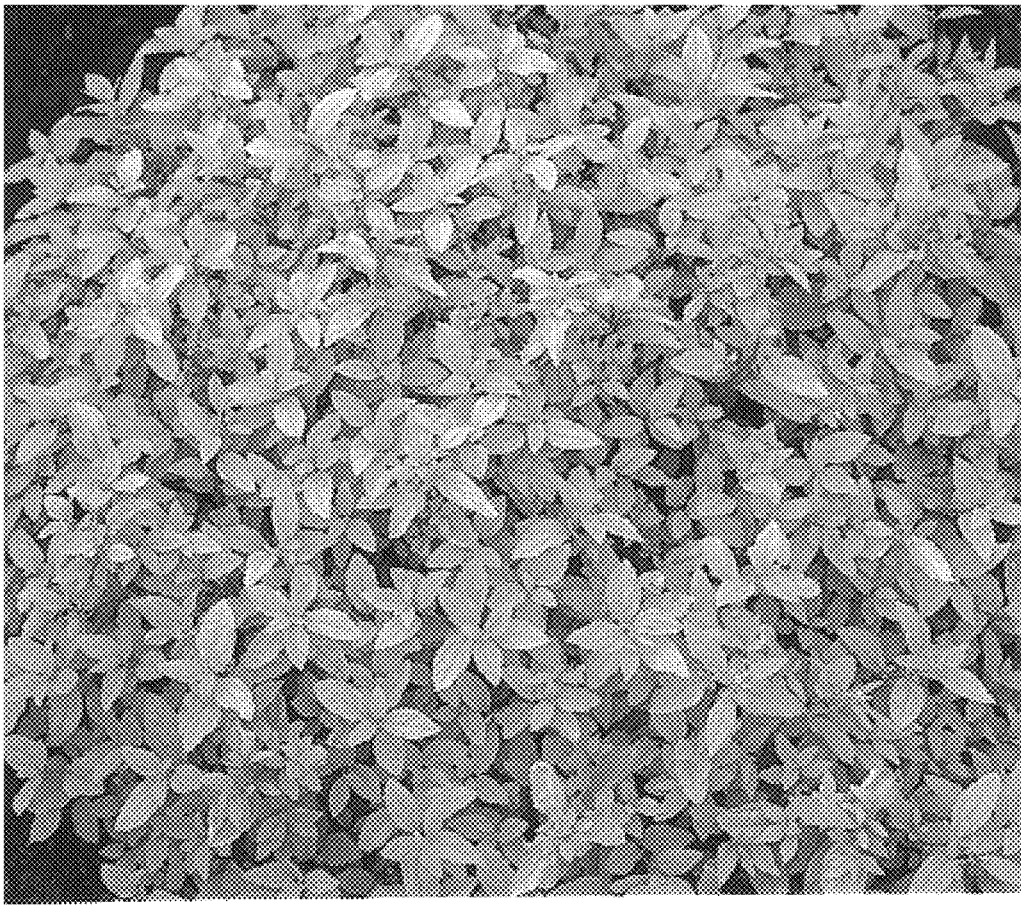
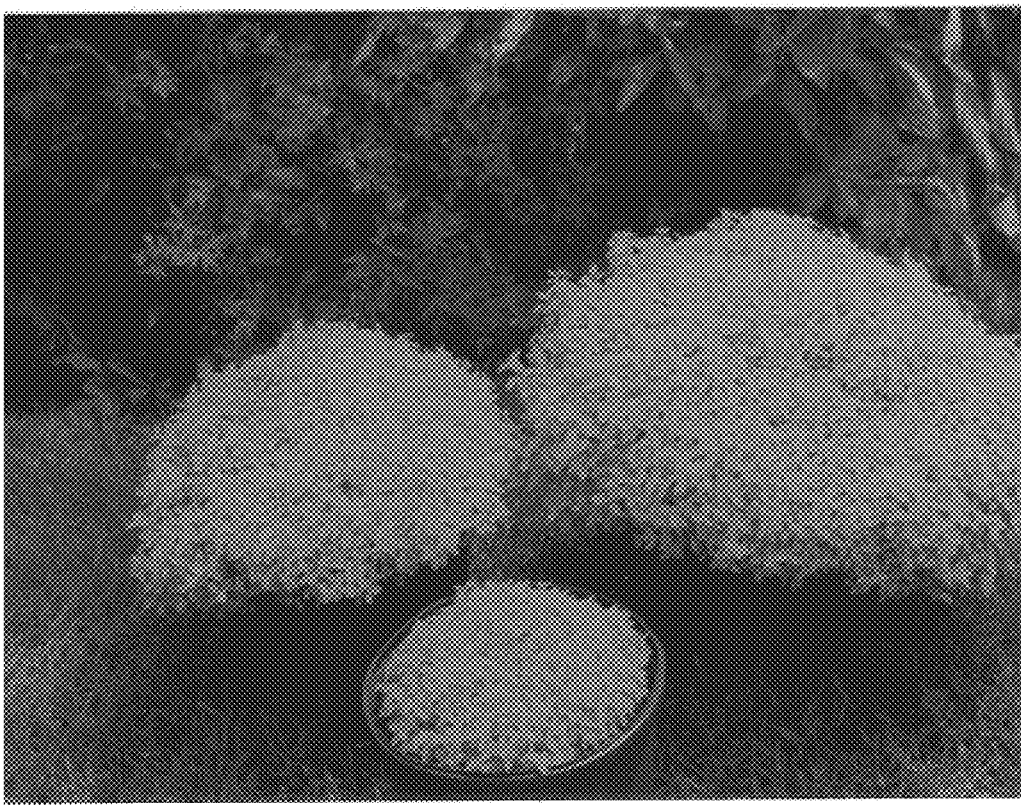

* * * * *